US006420598B1

(12) United States Patent
Weferling et al.

(10) Patent No.: US 6,420,598 B1
(45) Date of Patent: Jul. 16, 2002

(54) PROCESS FOR PREPARING ALKYLPHOSPHONIC ACIDS

(75) Inventors: Norbert Weferling, Hürth; Martin Sicken, Köln; Hans-Peter Schmitz, Brühl, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/591,712

(22) Filed: Jun. 12, 2000

(30) Foreign Application Priority Data

Jun. 18, 1999 (DE) .......................................... 199 27 787

(51) Int. Cl.[7] .................................................. C07F 9/30
(52) U.S. Cl. ............................................................ 562/8
(58) Field of Search ............................................... 562/8

(56) References Cited

U.S. PATENT DOCUMENTS

| | | | |
|---|---|---|---|
| 2,957,931 A | 10/1960 | Hamilton et al. | 260/403 |
| 3,488,368 A | 1/1970 | Spivack | 260/429.7 |
| 3,534,127 A | 10/1970 | Spivack | 260/968 |
| 3,563,948 A | 2/1971 | Spivack | 260/45.75 |
| 3,742,096 A | 6/1973 | Spivack | 260/953 |
| 3,812,222 A | 5/1974 | Kleiner et al. | |
| 3,912,654 A | 10/1975 | Heid et al. | 252/321 |
| 3,914,345 A | 10/1975 | Kleiner et al. | 260/970 |
| 4,036,811 A | 7/1977 | Noetzel et al. | 260/45.75 W |
| 4,208,322 A | 6/1980 | Sandler | 260/45.75 K |
| 4,321,187 A | 3/1982 | Granzow | 524/133 |
| 4,590,014 A | 5/1986 | Wolf et al. | 260/502.4 R |
| 4,632,741 A | 12/1986 | Wolf et al. | 204/157.73 |
| 4,740,332 A * | 4/1988 | Thottahil | |
| 4,939,285 A | 7/1990 | Weis et al. | 558/214 |
| 4,972,011 A | 11/1990 | Richardson et al. | 524/130 |
| 4,973,727 A | 11/1990 | Gainer et al. | 558/133 |
| 5,780,534 A | 7/1998 | Kleiner et al. | 524/133 |
| 6,207,736 B1 | 3/2001 | Nass et al. | 524/126 |

FOREIGN PATENT DOCUMENTS

| | | |
|---|---|---|
| DE | 2 043 520 | 3/1972 |
| EP | 0327496 | 8/1989 |
| EP | 0699708 | 3/1996 |
| ES | 8505520 | 5/1984 |
| FR | 1 558 606 A | 2/1969 |
| FR | 2 085 443 | 12/1971 |

OTHER PUBLICATIONS

"Phosphinsaure und deren Derivate," Dr. Felcht, vol. E2, 1982, pp. 123 ff.
CA:77:82165 abs of FR2085443 Jan. 1972.*
Journal of General Chemistry USSR by Nifantev et al 61 pp 83–92 year 1991.*
C.E. Griffin, H.J. Wells, Journal of Organic Chemistry, 24 (1959), p. 2049–2051.
JP 04283594 als Chemical Abstract 1993, 118, Nr. 59880.
SU 687079 als Chemical Abstract 1980, 92 Nr. 6695b.
Römpp–Lexikon Chemie, Hrsg, Jürgen Falbe und Manfred Regitz, Stuttgart, New York, Thieme Verlag, 1998, p. 3291.
E.E. Nifant'ev: "Acid catalysis in the hydrophosphorylation of olefins" Journal of General Chemistry USSR., vol. 50, No. 8/1,—Aug. 1980, pp. 1416–1423, XP002093427, New York US.
Chemical Abstract, vol. 69, No. 16, Oct. 14, 1968 Columbus, OH, US; abstract No. 067487, p. 6310; col. 2; XP002093429 & Petrov K.A.: "Dialkylphosphinic acids" KHIM. ORG. SOEDIN. FOSFORA, AKAD. NAUK SSSR, OTD. OBSHCH. TEKH. KHIM., 1967, PP. 181–186, SU. Synthesis of DI(n–octyl)phosphinic acid. Influence of the sulfuric acid in the phosphination of 1–octene with sodium hypophosphite, M. Martinez, C. Herranz, N. Miralles, & A. Sastre, AFINIDAD LIII, 466, 1996, pp. 404–406.
CA:107:25119 abs of ES532346 (6/85).
CA:107:176590 abs of Bull Chem Soc Jpn by Ohno 60 (8) pp 2945–51 (1987).
William C. Drinkard: "Some salts of symmetric phosphinic acids" Journal of the American Cehmical Society., Bd. 74, Nr. 21,–5. Nov. 1952 Seiten 5520–5521, XP002093391.
Chemical abstracts vol. 64 abstract No. 19661 g by Hoffmann (6/66).
Houben–Weyl, Methoden der organischen Chemie, vol. XII/1, 4th Edition, 1963, pp. 228ff.

* cited by examiner

*Primary Examiner*—Jean F. Vollano
(74) *Attorney, Agent, or Firm*—Susan S. Jackson; Scott E. Hanf

(57) ABSTRACT

The present invention relates to a process for the preparation of alkylphosphonic acids, which comprises reacting phosphorous acid ($H_3PO_3$) with short-chain olefins, and to the use of the products prepared by this process.

18 Claims, No Drawings

PROCESS FOR PREPARING ALKYLPHOSPHONIC ACIDS

BACKGROUND OF THE INVENTION

The present invention relates to a process for the preparation of alkylphosphonic acids and to the use of the products prepared by this process.

Alkylphosphonic acids are of great industrial importance and are widely employed, themselves or in the form of their salts, esters and anhydrides, in an extremely wide variety of areas of application. Examples of applications of alkylphosphonic acids are water softening, ore flotation, heavy-metal complexing and as starting materials for the preparation of, inter alia, flame retardants, pharmaceuticals and pesticides.

These compounds are usually prepared by complex multistage syntheses, for example by first preparing dialkyl phosphites from phosphorus trichloride by reaction with alcohols, subsequently adding these products onto olefins or carbonyl compounds, and converting the resultant phosphonic acid diesters into the phosphonic acids by hydrolysis with elimination of the alcohols previously employed.

This method causes considerable consumption of the alcohols employed as auxiliaries since undesired alkyl chlorides are formed in the reaction with phosphorus trichloride, and losses also occur during alcohol recycling. This and the multi-stage nature of the process have the consequence that the products prepared in this way can only be prepared in a complex and uneconomical manner and therefore cannot be employed for many possible applications.

Even the second industrially significant preparation method, in which the Michaelis-Arbusov reaction is used, is technically complex, starts from expensive starting materials (esters of phosphorous acid), causes unavoidable production of alkyl halides and requires subsequent hydrolysis.

The direct preparation of phosphonic acids from phosphorous acid has hitherto been restricted to the reaction with formaldehyde/ammonia to give aminomethylphosphonic acids and to the reaction with carbonyl compounds to give hydroxymethylphosphonic acids.

Attempts to react phosphorous acid with relatively long-chain olefins has resulted in low yields and considerable side-reactions [C. E. Griffin, H. J. Wells, J. Org. Chem. 24 (1959) 2049].

SUMMARY OF THE INVENTION

There is therefore a need for a process for the preparation of phosphonic acids which can be carried out in a simple manner and in which uniform products are obtained in high yield. A process of this type should also be significantly superior to the processes known hitherto in economic and environmental terms.

The invention thus has the object of providing a process for the preparation of phosphonic acids which avoids the above-mentioned disadvantages and can be carried out in one step, starting from simple, available starting materials.

This object is achieved by a process of the type mentioned at the outset which comprises reacting phosphorous acid ($H_3PO_3$) with short-chain olefins.

DESCRIPTION OF THE PREFERRED EMBODIMENTS

Under the reaction conditions, the short-chain olefins are gaseous.

The process according to the invention which gives the corresponding alkylphosphonic acids has considerable advantages over the processes known hitherto, since it proceeds in one step, does not use alcohols and does not produce any halogenated organic by-products. It is a direct reaction without the need for any intermediate steps.

The phosphorous acid is preferably reacted with olefins in the presence of a free-radical initiator.

The free-radical initiators employed are preferably azo compounds. The azo compounds are preferably cationic and/or non-cationic azo compounds.

The cationic azo compounds employed are preferably 2,2'-azobis(2-amidinopropane)dihydrochloride or 2,2'-azobis(N,N'-dimethyleneisobutyramidine)dihydrochloride.

The non-cationic azo compounds employed are preferably azobis(isobutyronitrile), 4,4'-azobis(4-cyanopentanoic acid) or 2,2'-azobis(2-methylbutyronitrile).

The free-radical initiators employed are preferably also peroxidic inorganic and/or peroxidic organic free-radical initiators.

The peroxidic inorganic free-radical initiators employed are preferably hydrogen peroxide, ammonium peroxodisulfate and/or potassium peroxodisulfate.

The peroxidic organic free-radical initiators employed are preferably dibenzoyl peroxide, di-tert-butyl peroxide and/or peracetic acid.

A broad selection of suitable free-radical initiators is given, for example, in Houben-Weyl, Supplementary Volume 20, in the chapter "Polymerization by free-radical initiation" on pages 15–74.

The free-radical initiators are preferably metered in continuously during the reaction.

The free-radical initiators are preferably metered in continuously during the reaction in the form of a solution in the solvent employed.

The olefins employed are preferably $C_2$- to $C_5$-olefins.

The olefins employed are preferably ethylene, propylene, 1-butene, 2-butene, 2-methyl-1-propene, 1-pentene, 2-pentene and/or 2-methyl-1-butene.

The reaction is preferably carried out at a temperature of from 40 to 200° C.

The reaction is particularly preferably carried out at a temperature of from 70 to 130° C.

The reaction is preferably carried out without solvents in the melt of the phosphorous acid.

However, the reaction is alternatively preferably carried out in the presence of a solvent.

The solvent is preferably acetic acid or ethyl acetate.

The reaction is preferably carried out under the pressure of the olefin employed.

The reaction is preferably carried out under a pressure of the olefin employed of from 1 to 20 bar.

Water is preferably added during or after the reaction.

In particular, the present invention also relates to a process in which phosphorous acid is reacted with ethylene in the presence of a free-radical initiator based on azo compounds or in the presence of a peroxidic free-radical initiator to give ethylphosphonic acid as the principal product.

In particular, the present invention also relates to a process in which phosphorous acid is reacted with propylene in the presence of a free-radical initiator based on azo compounds or in the presence of a peroxidic free-radical initiator to give propylphosphonic acid as the principal product.

The invention also relates to the use of the alkylphosphonic acids prepared in accordance with the invention for the preparation of organophosphorus compounds and derivatives.

The invention also relates to the use of the alkylphosphonic acids prepared in accordance with the invention as precursors for chemical synthesis.

The invention also relates to the use of the alkylphosphonic acids prepared in accordance with the invention as flame retardants or for the preparation of flame retardants.

The invention also relates to the use of the alkylphosphonic acids prepared in accordance with the invention as flame retardants in thermoplastic polymers, such as polyethylene terephthalate, polybutylene terephthalate or polyamide.

The invention also relates to the use of the alkylphosphonic acids prepared in accordance with the invention as flame retardants in thermosetting resins, such as unsaturated polyester resins, epoxy resins, polyurethanes or acrylates.

The desired phosphonic acids are obtained in high selectivity in extremely high yields. This is achieved in the process according to the invention by a constant concentration of the reactive phosphorous acid free radicals being generated by continuous metering of the free-radical initiator into the reaction mixture. These free radicals react with the short-chain olefins to give the phosphonic acids with virtually no side-reactions, since the olefin concentration in the liquid phase is low owing to their poor solubility in phosphorous acid or the solvents used. Side-reactions in which olefins react with themselves, for example via allyl free radicals, are thus greatly suppressed. On the other hand, the reaction is sufficiently fast on use of short-chain olefins since these have high diffusion rates from the gas phase into the liquid phase.

Reaction by-products which can occur, depending on the conditions, are small amounts of homologization products, such as, for example, hexylphosphonic acid from the double adduction of propylene onto phosphorous acid.

Further by-products which can be formed, in particular on use of relatively high reaction temperatures, are phosphonic acid anhydrides and, through olefin insertion into the P—O—H group, phosphonic acid esters. The latter by-products can be converted into the desired phosphonic acids by addition of small amounts of water toward the end of the reaction.

Unreacted phosphorous acid can be removed from the reaction product by customary methods, such as recrystallization.

EXAMPLES

The invention is explained by the examples below:

Example 1

Propylphosphonic Acid 6 kg (73 mol) of phosphorous acid were introduced into a 16 l twin-jacket pressure reactor made from steel enamel. After the phosphorous acid had been melted and heated to 100° C., propylene was introduced into the reactor via a reduction valve set to 4 bar until saturation had been achieved. A solution of 164 g (1 mol) of 2,2'-azobis (isobutyronitrile) in 3 l of glacial acetic acid was metered in at a temperature of from 100 to 110° C. over a period of 24 hours with constant stirring and with constant supply of propylene. The mixture was then allowed to react at 100° C. for a further 1 hour. The reactor was decompressed and cooled to room temperature, and the contents were analyzed. $^{31}$P-NMR analysis:

| | | |
|---|---|---|
| propylphosphonic acid: | 35.4 ppm | 80.2 mol % |
| hexylphosphonic acid: | 35.0 ppm | 4.2 mol % |
| propylphosphonic anhydride: | 25.3 ppm | 2.7 mol % |
| isopropyl propylphosphonate: | 38.8 ppm | 4.0 mol % |
| phosphorous acid: | 7.1 ppm | 7.9 mol % |
| unknown components: | | 1.0 mol % |

After addition of 100 ml of water, the reaction mixture was heated to the boil and freed from the solvents and catalyst decomposition products present in a rotary evaporator. 8.95 kg of propylphosphonic acid were obtained in this way in the form of a white solid having a melting range of from 35 to 45° C. The phosphonic acid content was >91%.

Example 2

Ethylphosphonic Acid 6 kg (73 mol) of phosphorous acid were introduced into a 16 l twin-jacket pressure reactor made from steel enamel. After the phosphorous acid had been melted and heated to 100° C., ethylene was introduced into the reactor via a reduction valve set to 6 bar until saturation had been achieved. A solution of 82 g (0.5 mol) of 2,2'-azobis (isobutyronitrile) (AIBN) in 600 ml of ethyl acetate was metered in at a temperature of from 100 to 110° C. over a period of 8 hours with constant stirring and with constant supply of ethylene. The ethylene pressure was subsequently increased to 10 bar, and a solution of a further 41 g (0.25 mol) of AIBN in 300 ml of glacial acetic acid was metered in at the same temperature over a period of 4 hours. 100 ml of water were then metered in,. and the mixture was then allowed to react at 100° C. for a further 1 hour. The reactor was decompressed and cooled to room temperature, and the contents were analyzed. $^{31}$P-NMR analysis:

| | | |
|---|---|---|
| ethylphosphonic acid: | 37.1 ppm | 92.2 mol % |
| butylphosphonic acid: | 35.7 ppm | 6.9 mol % |
| phosphorous acid: | 6.9 ppm | 0.7 mol % |
| unknown components: | | 0.2 mol % |

The reaction mixture was freed from solvents and initiator residues present in a rotary evaporator. 8.2 kg of ethylphosphonic acid (99% yield; purity about 90%; remainder butylphosphonic acid, ethylphosphonic anhydride) were obtained in this way in the form of a white solid. The phosphorus analysis gave 27.3% of P (theor.: 27.7%).

What is claimed is:

1. A process for the preparation of alkylphosphonic acids, which comprises reacting phosphorous acid with short-chain olefins, wherein the reaction is carried out without a solvent in a melt of the phosphorous acid and wherein the olefins employed are ethylene, propylene, 1-butente, 2-butene, 2-methyl-1-propene, 1-pentene, 2-pentene and/or 2-methyl-1-butene.

2. A process as claimed in claim 1, wherein the reaction is carried out in the presence of a free-radical initiator.

3. A process as claimed in claim 2, wherein the free-radical initiators employed are azo compounds.

4. A process as claimed in claim 3, wherein the azo compounds are cationic and/or non-cationic azo compounds.

5. A process as claimed in claim 4, wherein the cationic azo compounds employed are 2,2'-azobis(2-amidinopropane)dihydrochloride or 2,2'-azobis-(N,N'-dimethyleneisobutyramidine)dihydrochloride.

6. A process as claimed in claim 4, wherein the non-cationic azo compounds employed are azobis (isobutyronitrile), 4,4'-azobis(4-cyanopentanoic acid) or 2,2'-azobis(2-methylbutyronitrile).

7. A process as claimed in claim 2, wherein the free-radical initiators employed are peroxidic inorganic and/or peroxidic organic free-radical initiators.

8. A process as claimed in claim 7, wherein the peroxidic inorganic free-radical initiators employed are hydrogen peroxide, ammonium peroxodisulfate and/or potassium peroxodisulfate.

9. A process as claimed in claim 7, wherein the peroxidic organic free-radical initiators employed are dibenzoyl peroxide, di-tert-butyl peroxide and/or peracetic acid.

10. A process as claimed in claim 2, wherein the free-radical initiators are metered in continuously during the reaction.

11. A process as claimed in claim 1, wherein the olefins employed are $C_2$–$C_5$-olefins.

12. A process as claimed in claim 1, wherein the reaction is carried out at a temperature of from 40 to 200° C.

13. A process as claimed in claim 1, wherein the reaction is carried out at a temperature of from 70 to 130° C.

14. A process as claimed in claim 1, wherein the reaction is carried out under pressure.

15. A process as claimed in claim 14, wherein the reaction is carried out under a pressure of from 1 to 20 bar.

16. A process as claimed in claim 1, wherein water is added during or after the reaction.

17. A process as claimed in claim 1, wherein the phosphorous acid is reacted with ethylene in the presence of a free-radical initiator based on azo compounds or in the presence of a peroxidic free-radical initiator to give ethylphosphonic acid as the principal product.

18. A process as claimed in claim 1, wherein the phosphorous acid is reacted with propylene in the presence of a fee-radical initiator based on azo compounds or in the presence of a peroxidic free-radical initiator to give propylphosphonic acid as the principal product.

* * * * *